United States Patent [19]

Ottow et al.

[11] Patent Number: 4,814,327

[45] Date of Patent: Mar. 21, 1989

[54] 11 β-(4-ISOPROPENYLPHENYL)ESTRA-4,9-DIENES, THEIR PRODUCTION, AND PHARMACEUTICAL PREPARATIONS CONTAINING SAME

[75] Inventors: Eckhard Ottow; Rudolf Wiechert; Günter Neef; Sybille Beier; Walter Elger; David Henderson, all of Berlin, Fed. Rep. of Germany

[73] Assignee: Schering Aktiengesellschaft, Berlin and Bergkamen, Fed. Rep. of Germany

[21] Appl. No.: 77,359

[22] Filed: Jul. 24, 1987

[30] Foreign Application Priority Data

Jul. 25, 1986 [DE] Fed. Rep. of Germany ....... 3625315

[51] Int. Cl.$^4$ .................... A61K 31/56; C07J 1/00
[52] U.S. Cl. .................... 514/179; 514/181; 514/182; 260/397.45; 260/397.47; 260/397.5
[58] Field of Search ........... 260/397.45, 397.47, 260/397.3, 397.4, 397.5; 514/177, 178, 179, 182, 181

[56] References Cited

U.S. PATENT DOCUMENTS

| | | |
|---|---|---|
| 4,386,085 | 5/1983 | Teutsch et al. . |
| 4,447,424 | 5/1984 | Teutsch et al. . |
| 4,519,946 | 5/1985 | Teutsch et al. . |
| 4,536,401 | 8/1985 | Neef et al. . |
| 4,540,686 | 9/1985 | Philibert et al. . |
| 4,547,493 | 10/1985 | Teutsch et al. ............ 260/397.45 X |
| 4,609,651 | 9/1986 | Rohde et al. . |

FOREIGN PATENT DOCUMENTS

| | | |
|---|---|---|
| 0116974 | 8/1984 | European Pat. Off. .............. 540/41 |
| 2801417 | 7/1978 | Fed. Rep. of Germany ...... 260/397 |
| 3231827 | 3/1984 | Fed. Rep. of Germany ....................... 260/397.47 |
| 8210205 | 12/1983 | France . |

Primary Examiner—Helen M. S. Sneed
Assistant Examiner—James Saba
Attorney, Agent, or Firm—Millen & White

[57] ABSTRACT

11 β-(4-isopropenylphenyl)-estra-4,9-dienes of general Formula I

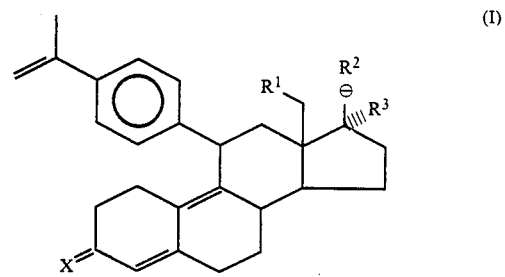

wherein

X is an oxygen atom or a hydroxyimino grouping N~OH, $R^1$ is a hydrogen atom or a methyl group, $R^2$ is a hydrogen atom or an acyl residue of 1–10 carbon atoms, $R^3$ is a hydrogen atom, the cyanomethyl group, —(CH$_2$)$_n$—, CH$_2$Z, —CH=CH—(CH$_2$)$_m$Z or —C≡C—Y wherein n=0 to 5 and m=1 to 4, Z meaning a hydrogen atom or the OR$^4$ group with R$^4$ meaning a hydrogen atom, an alkyl or alkanoyl group each of 1–4 carbon atoms, and Y meaning a hydrogen, chlorine, fluorine, iodine or bromine atom, an alkyl, hydroxyalkyl, alkoxyalkyl or acyloxyalkyl group each of 1–4 carbon atoms in the alkyl or acyl residue, possess antiprogestational activity.

18 Claims, No Drawings

11 β-(4-ISOPROPENYLPHENYL)ESTRA-4,9-DIENES, THEIR PRODUCTION, AND PHARMACEUTICAL PREPARATIONS CONTAINING SAME

BACKGROUND OF THE INVENTION

The invention relates to novel 11 β-(4-isopropenylphenyl)-4,9-estradienes, processes for their production, and pharmaceutical preparations containing same.

11 β-(4-Isopropylphenyl)-4,9-estradienes and their antiglucocorticoid activity are known from U.S. Pat. No. 4,540,686.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing the compounds of this invention characterized by Formula I

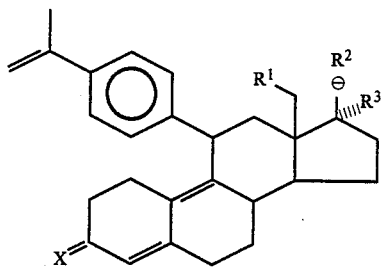

wherein

X is an oxygen atom or a hydroxyimino grouping N~~~OH, $R^1$ is a atom or a methyl group, $R^2$ is a hydrogen atom or an acyl residue of 1–10 carbon atoms, $R^3$ is a hydrogen atom, the cyanomethyl group, —(CH$_2$)$_n$—CH$_2$Z, —CH=CH—(CH$_2$)$_m$Z or —C≡C—Y wherein n=0 to 5 and m=1 to 4, Z meaning a hydrogen atom or the OR$^4$ group with R$^4$ meaning a hydrogen atom, an alkyl or alkanoyl group each of 1–4 carbon atoms, and Y meaning a hydrogen, chlorine, fluorine, iodine or bromine atom, an alkyl, hydroxyalkyl, alkoxyalkyl or acyloxyalkyl group each of 1–4 carbon atoms in the alkyl or acyl residues.

Suitable alkyl, alkanoyl and alkoxy groups for R$^4$ and Y contain 1–4 carbon atoms wherein the methyl, ethyl, propyl, acetyl propionyl, butyryl, methoxy and ethoxy groups are preferred also suitable being butyl, formyl, propoxy and butoxy and all isomers thereof. When R$^2$ stands for an acyl residue, then the formyl, acetyl, propionyl, butyryl and benzoyl groups are preferred. The foregoing alkyl portions and acyl portions are also suitable for use in the other groups for Formula I, e.g., acyloxyalkyl for Y, etc.

Among the general alkenyl residues, the propenyl and butenyl groups are preferred, which can be present in the E or Z configuration, i.e., if R$^3$ stands for —CH=CH—(CH$_2$)$_m$Z, then m is to be preferably 1 or 2.

Preferred compounds of general Formula I are:

11 β-(4-isopropenylphenyl)-17 β-hydroxy-4,9-estradien-3-one

11 β-(4-isopropenylphenyl)-17 β-hydroxy-17-(prop-1-ynyl)-4,9-estradien-3-one

11 β-(4-isopropenylphenyl)-17 β-hydroxy-17-(prop-1(Z)-enyl)-4,9-estradien-3-one

11 β-(4-isopropenylphenyl)-17 β-hydroxy-17-(3-hydroxyprop-1(Z)-enyl)-4,9-estradien-3-one 11 β-(4-isopropenylphenyl)-17 β-hydroxy-17-(4-hydroxybut-1(Z)-enyl)-4,9-estradien-3-one 11 β-(4-isopropenylphenyl)-17 β-hydroxy-18-methyl-4,9-estradien-3-one 11 β-(4-isopropenylphenyl)-17 β-hydroxy-18-methyl-17-(prop-1-ynyl)-4,9-estradien-3-one 11 β-(4-isopropenylphenyl)-17 β-hydroxy-18-methyl-17-(prop-1(Z)-enyl)-4,9-estradien-3-one 11 β-(4-isopropenylphenyl)-17 β-hydroxy-18-methyl-17-(3-hydroxyprop-1(Z)-enyl)-4,9-estradien-3-one 11 β-(4-isopropenylphenyl)-17 β-hydroxy-18-methyl-17-(4-hydroxybut-1(Z)-enyl)-4,9-estradien-3-one 11 β-(4-isopropenylphenyl)-17 β-hydroxy-17-(3-hydroxypropyl)-4,9-estradien-3-one 11 β-(4-isopropenylphenyl)-17 β-hydroxy-18-methyl-17-(3-hydroxypropyl)-4,9-estradien-3-one 11 β-(4-isopropenylphenyl)-17 β-hydroxy-17-methoxymethyl-4,9-estradien-3-one 11 β-(4-isopropenylphenyl)-17 β-hydroxy-17-cyanomethyl-4,9-estradien-3-one.

The novel 11 β-(4-isopropenylphenyl)-4,9estradienes of general Formula I can be prepared according to this invention by a process characterized in that, in a manner known per se, a compound of general Formula II

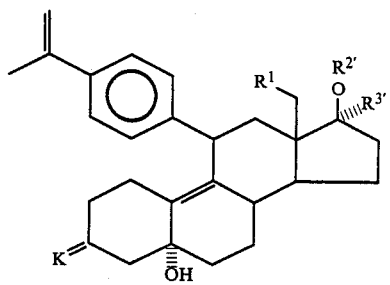

wherein

R$^1$ has the meanings given above,

K is an acidically hydrolyzable keto blocking group, and

R$^{2'}$ and R$^{3'}$ have the same meanings as R$^2$ and R$^3$ wherein any present hydroxy groups are optionally blocked, is subjected to the effect of an acidic agent capable of liberating the blocked function(s) and of selectively splitting off the 5 α-hydroxy group with simultaneous formation of the 4(5)-double bond, and optionally free hydroxy groups in the 17-position and/or in R$^{3'}$ are esterified or free hydroxy groups in R$^{3'}$ are etherified.

The starting compounds of general Formula II can be prepared from the epoxides of general Formula III

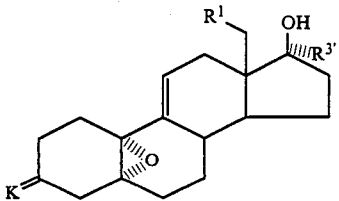

(German Laid-Open Application DE No. 33 47 126 A 1) wherein $R^1$ and K have meanings given above, K representing, in particular, a form of the ketal, thioketal, oxime or methyloxime, and $R^{3''}$ is a hydrogen atom or —C≡C—(CH$_2$)$_m$—OU with m=1 to 4 and U meaning an acid-instable hydroxy blocking group.

Introduction of the 11 β-(4-isopropenylphenyl) residue with formation of the Δ9,10-5α-hydroxy structural element takes place conventionally in analogy to the precesses set forth in European Patent Applications Publication Nos. 57,115 and 110,434 by Cu(I)-catalyzed Grignard reaction with the corresponding arylmagnesium halide (Tetrahedron Letters 1979: 2051) or by reaction of the corresponding homo- or heterocuprate of the types Ar$_2$-CuLi and Ar$_2$Cu(CN)Li, etc. (J. Amer. Chem. Soc. 103: 7672 [1981]).

All starting materials are conventional or conventionally preparable from known starting materials.

The compounds obtained—optionally after conventional conversion of the C-17 substituent $R^{3''}$ into the C-17 substitution pattern of the lastly desired meaning of $R^2$ and $R^3$ in the final product of general Formula I—exhibiting general Formula II

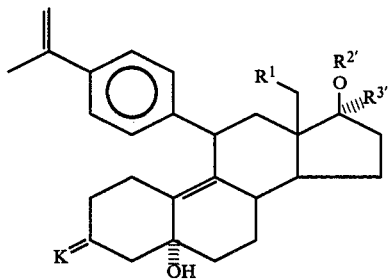

wherein $R^1$ and K have the above-mentioned meanings, $R^{2'}$ and $R^{3'}$ have the same meanings as $R^2$ and $R^3$ wherein any present hydroxy groups are optionally blocked, are subsequently treated, for the selective splitting off of water with formation of the 4(5)-double bond and for the simultaneous removal of any present blocking groups, with an acid or an acidic ion exchanger. The acid treatment takes place conventionally by dissolving the compound of Formula II in a water-miscible solvent, such as aqueous methanol, ethanol or acetone, and treating the solution with catalytic amounts of a mineral or sulfonic acid, such as hydrochloric acid, sulfuric acid, phosphoric acid, perchloric acid or p-toluenesulfonic acid, or an organic acid, such as acetic acid, until water has been split off and blocking groups have been removed. The reaction, proceeding at temperatures of 0° C. to 100° C., can also be performed with an acidic ion exchanger. The course of the reaction can be observed with analytical methods, e.g., by thin-layer chromatography of withdrawn samples.

The blocking groups covered in general Formulae II and III by K and $R^{3'}$ and K and $R^{3''}$, respectively, are groups readily cleavable in an acidic medium, for example the ethylenedioxyketal, ethylenedithioketal, 2,2-dimethyltrimethylenedioxyketal, hydroxyimino, methoxyimino, tetrahydropyranyl, methoxymethyl, or methoxyethyl group.

Substitution of the $R^{3'}$ hydrogen atom by the other residues included for $R^{3'}$ takes place according to the usual methods of construction of C-17 side chains by nucleophilic addition to the 17-ketone, obtained by Oppenauer oxidation of the C-17-hydroxy function, and by subsequent reactions ("Terpenoids and Steroids", Specialist Periodical Report, The Chemical Society, London, vol. 1–12).

Nucleophilic addition of HC≡CY wherein Y means hydrogen, alkyl of 1–4 carbon atoms or halogen takes place with the aid of a compound of the general formula MC≡CY wherein Y has the above meanings and M is an alkali metal. The organometallic compound is produced by treatment of the corresponding acetylene with a base. In this process, the alkali acetylide can be generated from the corresponding acetylene, for example, by treatment with butyllithium or methyllithium in a suitable solvent, preferably dialkyl ether, tetrahydrofuran, dioxane, benzene or toluene.

For preparing the 17-chloroethynyl compound, the organometallic chloroethynyl compound is formed in situ from 1,2-dichloroethylene and an ethereal alkali metal solution, such as, for example, methyllithium or butyllithium solution, and reacted with the 17-ketone in solvents, such as tetrahydrofuran or diethyl ether. 17-Haloethynyl compounds can also be produced by halogenation of the corresponding ethynyl aduct (Angew. Chemie 96:720 [1984]).

The introduction of 3-hydroxypropyne and, respectively, -propene in the 17-position takes place by reaction of the 17-ketone with the dianion of propargyl alcohol, for example the dipotassium salt of propargyl alcohol generated in situ, to obtain the 17-(3-hydroxy-prop-1-ynyl)-17 β-hydroxy compound, or with metallized derivatives of 3-hydroxypropyne, for example with 1-lithium-3-(tetrahydropyran-2'-yloxy)prop-1-yn-1-ide, to obtain the 17-[3-(tetrahydropyran-2'-yolxy)-prop-1-ynyl]-17 β-hydroxy compound which can subsequently be hydrogenated. This is accomplished, for example, by hydrogenation at room temperature and under normal pressure in solvents, such as methanol, ethanol, propanol, tetrahydrofuran, or ethyl acetate with the addition of modified noble metal catalysts, such as platinum or palladium.

Introduction of the homologous hydroxyalkyne and hydroxyalkene groups takes place correspondingly with homologs of propargyl alcohol.

The compounds with the Z-configured double bond in the hydroxyalkenyl side chains are prepared by hydrogenation of the corresponding acetylenic structures with a deactivated noble metal catalyst (J. Fried, J. A. Edwards: Organic Reactions in Steroid Chemistry, Van Nostrand Reinhold Company, 1972, p. 134; H. O. House: Modern Synthetic Reactions 1972, p. 19). Examples for suitable deactivated noble metal catalysts are 10% palladium on barium sulfate in the presence of an amine or 5% palladium on calcium carbonate with the addition of lead(II) acetate. Hydrogenation is terminated after absorption of one equivalent of hydrogen.

The compounds with the E-configured double bond in the alkenyl side chains are formed by reduction of the acetylenic structures in a manner known per se. Quite a number of methods are described in the literature for the conversion of alkynes into transolefins, for example the reduction with lithium aluminum hydride (J. Amer. Chem. Soc. 89:4245 [1967]), with diisobutyl aluminum hydride and methyllithium (J. Amer. Chem. Soc. 89:5085 [1967]), or chromium(II) sulfate in the presence of water or dimethylformamide in a weakly acidic medium (J. Amer. Chem. Soc. 86:4358 [1964]), as well as generally reduction by the effect of transition metal compounds with a change in the oxidation stage.

Introduction of 3-hydroxypropane in the 17-position takes place by reacting the 17-ketone with metallized derivatives of 3-halopropanols, wherein the hydroxy group is present in the metallizing step as the alcoholate (Tetrahedron Letters 1978:3013) or as a blocked function, to the 17-(3-hydroxypropyl)-17 β-hydroxy compound or to the compound blocked on the terminal hydroxy group. The same blocking groups are suitable as have been recited above for $R^{3'}$ and $R^{3''}$, respectively. Introduction of the homologous hydroxyalkane groups takes place correspondingly with homologs of the 3-halopropanols.

The construction of the 17-cyanomethyl side chain takes place conventionally from the 17-ketone, for example via the 17-spiroepoxide and cleavage of the spiroepoxide with HCN according to Z. Chem. 18:259 (1978).

Free hydroxy groups in the 17-position and in the residues standing for $R^{3'}$ can be conventionally esterified or etherified.

The novel compounds of general Formula I are valuable pharmaceuticals. Thus, they exhibit strong affinity to the gestagen receptor without themselves showing gestagen activity. They are competitive antagonists of progesterone (antiprogestogens) and are suitable for triggering abortion since they displace progesterone, necessary for maintaining pregnancy, from the receptor. They are, therefore, valuable and of interest with respect to their use for postcoital fertility control. They can also be used against gynaecological disorders, e.g., endometriosis, dysmenorrhea, neoplastic diseases of the mammary gland and for inducing menstruation, and for initiating labor. Furthermore, they can be employed for the treatment of carcinomas depending on hormones. For example, various tumors of the genital tract and the mammary glands, and meningiomas are known to possess receptors for ovarian hormones such as estrogens and progesterone. The progression of the growth of these tumors can be fovorably influenced by antigestagen treatment per this invention.

The compounds of general Formula I according to this invention also exhibit antiglucocorticoid activity and thus can likewise be utilized as medicines for the therapy of corticoid-induced disorders (e.g., glaucoma) as well as for combating side effects occurring in the long-term treatment with glucocorticoids (e.g. Cushing's syndrome). Therefore, they are capable of combating the disturbances caused by supersecretion of the glucocorticoids, above all adipositas, arteriosclerosis, hypertension, osteoporosis, diabetes, as well as insomnia.

When using the compounds of this invention for their antiglucocorticoid efficacy, in a preferred aspect, they will be used to treat conditions for which an antiprogestogenic effect is very well tolerated, e.g., Cushing's disease, glaucoma, etc.

It has also been found that the novel compounds of general Formula I show, surprisingly, not only very good antiprogestational and antiglucocorticoid effects, but also exhibit a separation of the two effects.

For characterizing the antiprogestational activity, the abortive efficacy was determined. The tests were performed on female rats weighing about 200 g. After mating had taken place, the beginning of pregnancy was ascertained by detection of sperm in vaginal smears. The day of sperm detection is considered day 1 of gravidity (=d1 p.c. (post coitus)).

Treatment of the animals with the particular compound to be tested and, respectively, with the solvent took place after nidation of the blastocysts from d5 p.c. to d7 p.c. On d9 p.c., the animals were sacrificed and the uteri examined for implants and resorption sites. Photographs were prepared of all uteri. The absence of implants was assessed as abortion.

The test compounds were dissolved in a benzyl benzoate-castor oil mixture (ratio 1+9). The vehicle volume per individual dose was 0.2 ml. Treatment was performed subcutaneously (s.c.).

The superiority of the compounds of this invention was demonstrated by comparing the biological properties of the compound of this invention 17-(3-hydroxyprop-1(Z)-enyl)-17 β-hydroxy-11 β-(4-isopropenylphenyl)-4,9-estradien-3-one (A); 11 β-(4-dimethylaminophenyl)-17 β-hydroxy-17 -(propyn-1-yl)-4,9(10)-estradien-3-one RU 38486 (B), described in EP No. 82400025.1 (U.S. Pat. Nos. 4,386,085, 4,447,424 and 4,519,946); 11 β-(4-dimehylaminophenyl)-17 β-hydroxy-17 -(3-hydroxypropyl)-4,9(10)-estradien-3one (C), described in EP No. 84101721.3 (U.S. Pat. No. 4,536,401); and 11 β-(4-dimethylaminophenyl)-17 β-hydroxy-17 -(3-hydroxyprop-1(Z)-enyl)-4,9(10)-estradien-3-one (D), described in EP No. 84730147.0 (U.S. Pat. No. 4,609,651).

TABLE

| Abortion Tests on Gravid Rats | | |
|---|---|---|
| Compound | Dose mg/Animal/Day s.c. | Abortion Rate n - Abortion Positive/ n - Total |
| A | 3.0 | 4/4 |
|  | 1.0 | 4/4 |
|  | 0.3 | 4/4 |
| B | 3.0 | 4/4 |
|  | 1.0 | 2/4 |
|  | 0.3 | 0/4 |
| C | 10.0 | 4/4 |
|  | 3.0 | 4/4 |
|  | 1.0 | 0/4 |
| D | 3.0 | 4/4 |
|  | 1.0 | 4/4 |
|  | 0.3 | 0/4 |

It can be seen from the table that, with a dose of 0.3 mg, only compound (A) according to this invention is fully effective abortively, i.e. this compound is more efficacious by a factor of 3–10 than the compounds of the state of the art.

To characterize the antiglucocorticoid effect, the effectiveness of the compounds of this invention on tyrosine aminotransferase was determined. The test system is based on measuring the activity of liver enzyme tyrosine aminotransferase (TAT) in cultures of RHC (rat hepatoma cells) cells. The enzyme catalyzes the first step of metabolizing of tyrosine and can be induced in the liver as well as in hepatoma cells by glucocorticoids. The activity can readily be measured in raw extracts (Granner and Tomkins [1970], Meth. Enzymol. 15:633). The enzyme transfers the amino group from tyrosine to 2-oxoglutaric acid. During this process, glutamic acid and p-hydroxyphenylpyruvate are formed. In alkaline solution, the more stable p-hydroxybenzaldehyde is formed from p-hydroxyphenylpyruvate, with an absorption measured at 331 nm. The TAT activity in RHC cells shows a dose-dependent induction with cortisol (maximum activity at $10^{-6}$ M) or dexamethasone (maximum activity at $10^{-7}$ M). The activity can be stimulated beyond the basic value by a factor of 4–6. Simultaneous treatment with corticoid and antiglucocorticoid leads to a decrease in TAT activity.

Compound (A) according to the invention shows, in this test, 2% of the activity of RU 38486 (B), a compound to be considered as the standard (7th Int. Congress of Endocrinology July 1–7, 1984, Quebec City, Canada; Excerpta Medica, Amsterdam-Oxford-Princeton).

Since compound (A) shows a progestational activity which is ten times stronger than that of (B), the result is thus a marked dissociation of the antiglucocorticoid and antiprogestational properties. A typical dosage unit for any use of this invention contains about 1–100 mg of active compound(s). The dose of the compounds of this invention is approximately 1–10,000 mg per day in the case of human patients. For the antiprogestational utilities, the general dosage range is 1–1000 mg, preferably 50–500 mg and the administration is analogous to the known antiprogestational agent (RU 38486). For the antiglucocordicoidal activity, the typical dosage range is 10–10,000, preferably 50–1000 mg, and the administration is analogous to the known antiglucocorticoidal agent (RU 38486). The precise dosage for a given patient will be conventionally determined according to the usual considerations including the condition of the patient, the choice of the specific compound, etc., especially in conjunction with a conventional pharmacological protocol, e.g., one discussed above.

Another outstanding property of the compounds of this invention is their metabolic stability which is high compared with prior-art compounds. Accordingly, the invention also relates to medicinal agents for treating mammals including humans, based on the pharmaceutically acceptable compounds of general Formula I, i.e. compounds that are nontoxic in the doses utilized, and optionally the customary auxiliary agents and excipients.

The compounds of this invention can be processed by conventional methods of galenic pharmacy into pharmaceutical preparations for enteral, percutaneous, parenteral or local administration. They can be administered in the form of tablets, dragees, gelatin capsules, granules, suppositories, implants, injectable sterile, aqueous or oily solutions, suspensions or emulsions, ointments, creams, and gels. The active agent or agents can be mixed with the auxiliary materials customary in galenic pharmacy, such as, for example, gum arabic, talc, amylose, mannitol, methylcellulose, lactose, tensides, such as "Tweens" or "Myrj", magnesium stearate, aqueous or nonaqueous vehicles, paraffin derivatives, surfactants, dispersion agents, emulsifiers, preservatives, and flavoring materials for improving taste (e.g. ethereal oils). Accordingly, the invention also concerns pharmaceutical compositions containing as the active ingredient at least one compound according to this invention.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all application, patents and publications, if any, cited above and below are hereby incorporated by reference.

EXAMPLE 1

17-(3-Hydroxyprop-1(Z)-enyl)-17β-hydroxy-11β-(4-isopropenylphenyl)-4,6-estradien-3-one A solution of 2.21 g (3.49 millimoles) of 17-[3-(tetrahydropyran-2-yloxy)prop-1(Z)-enyl]-11β-(4-isopropenylphenyl)-3,3-(2,2-dimethyltrimethylenedioxy)-9-estrene-5α,17β-diol in 20 ml of 70% aqueous acetic acid is stirred for 60 minutes at 50° C. After cooling, the mixture is poured into ice water, neutralized by adding aqueous ammonia solution, and extracted with dichloromethane. Chromatography of the crude product on silica gel with a mixture of ethyl acetate/hexane yields 1.02 g of the desired compound. $[\alpha]_D^{25} = +207°$ (c=0.50; CHCl$_3$).

The starting material is prepared as follows:

(a) At 40° C., a solution of 7.69 g (39 mmol) of 1-bromo-4-isopropenylbenzene (Chem. Ber. 55: 3406, 1922) in 40 ml of absolute THF is added to a suspension of 0.95 g (39 mmol) of magnesium in 10 ml of absolute tetrahydrofuran (THF). After the magnesium has been completely dissolved, the mixture is cooled to +5° C., and 100 mg (1 mmol) of copper chloride is added to the reaction solution. The solution is stirred for 15 minutes and then, at 5° C., a solution of 2 g (3.9 mmol) of 17-[3-(tetrahydropyran-2-yloxy)prop-1-ynyl]-5α,10α-epoxy-3,3-(2,2-dimethyltrimethylenedioxy)-9(11)-estren-17β-ol in 20 ml of absolute THF is added dropwise thereto. After this step, the reaction mixture is allowed to gradually warm up to room temperature overnight, then it is poured into a mixture of ice water/aqueous ammonia solution, and extracted with ethyl acetate. The resultant oily crude product is chromatographed with ethyl acetate/hexane on aluminum oxide (Merck, stage III, neutral), thus obtaining 2.4 g of 17-[3-(tetrahydropyran-2-yloxy)prop-1-ynyl]-11β-(4-isopropenylphenyl)-3,3-(2,2-dimethyltrimethylenedioxy)-9-estrene-5α,17β-diol.

$^1$H-NMR (CDCl$_3$): δ=0.47 ppm (s,3H,H-18); 2.15 (s,3H, CH$_3$-olefin.); 4.8 (s [broad], 1H,H-THP-ether); 5.05 and 5.4 (each s, each 1H,H-olefin.).

(b) A solution of 2.35 g (3.73 mmol) of the product obtained in (a) in 37 ml of ethanol is hdyrogenated, after adding 2.4 ml of pyridine and 235 mg of palladium/barium sulfate (10% Pd) at room temperature and under normal pressure. After hydrogen absorption has ceased, the mixture is filtered off from the catalyst and the filtrate is concentrated, thus obtaining 2.2 g of 17-[3-(tetrahydropyran-2-yloxy)prop-1(Z)-enyl]-11β-(4-isopropenylphenyl)-3,3-(2,2-dimethyltrimethylenedioxy)-9-estrene-5α,17β-diol.

$^1$H-NMR (CDCl$_3$): δ=0.49 ppm (s,3H,H-18); 2.15 (s,3H, CH$_3$-olefin.); 4.8 (s [broad], 1H,H-THP-ether); 5.05 and 5.38 (each s, each 1H, H-olefin.); 5.5–5.8 (m,2H,H-olefin. C-20 and C-21).

EXAMPLE 2

17-(4-Hydroxybut-1(Z)-enyl)-17β-hydroxy-11β-(4-isopropenylphenyl)-4,9-estradien-3-one Analogously to the acidic cleavage described in Example 1, 2.5 g of 17-(4-hydroxybut-1(Z)-enyl)-11β-(4-isopropenylphenyl)-3,3-(2,2-dimethyltrimethylenedioxy)-9-estrene-5α,17β-diol yields 1.28 g of the desired compound. $[\alpha]_D^{25} = +222°$ (CHCl$_3$; c=0.505).

The starting material is prepared as follows:

(a) Under a protective gas, 13.9 g of magnesium filings are combined with 175 ml of absolute tetrahydrofuran and mixed, in succession, with 0.5 ml of dibromoethane and 96 g of 90% strength 1-chloro-4-isopropenylbenzene, dissolved in 500 ml of absolute tetrahydrofuran. The reaction mixture is then heated to reflux until the Grignard reagent has been completely formed. Thereafter the solution is cooled to 0° C., and combined with 1.6 g of copper(I) chloride and then gradually with a solution of 42.5 g of 5α-10α-epoxy-3,3-(2,2-dimethyltrimethylenedioxy)-9(11)-estren-17β-ol in 250 ml of absolute tetrahydrofuran. The reaction mixture is gradually warmed under agitation overnight to room temperature, then cooled to 0° C. and mixed with 250 ml of saturated ammonium chloride solution. The organic phase is separated from the aqueous phase and the latter extracted repeatedly with ethyl acetate. The combined organic phases are washed with saturated sodium chloride solution, dried over sodium sulfate, and concentrated under vacuum. The residue is chromatographed with hexane/ethyl acetate on aluminum oxide (neutral, stage III), thus isolating 29.6 g of 11β-(4-isopropenylphenyl)-3,3-(2,2-dimethyltrimethylenedioxy)-9-estrene-5α,17β-diol as a white foam.

$^1$H-NMR (CD$_2$Cl$_2$): δ=0.33 ppm (s,3H,H-18); 2.13 (s,3H, CH$_3$-olefin.); 5.03 (s,1H,H-olefin.); 5.39 (s, 1H,H-olefin.); 7.1–7.5 (m,4H, H-aromat.).

(b) Under a protective gas, 29 g of the compound obtained in (a) is dissolved in 600 ml of absolute toluene and combined, in succession, with 16 g of aluminum triisopropylate and 118 ml of cyclohexanone. The reaction mixture is then heated to reflux, thus separating about one-third of the toluene via a water trap. After completing the reaction (thin-layer control), the reaction solution is cooled to room temperature and mixed with saturated sodium bicarbonate solution. The thus-formed suspension is filtered off over "Celite" and the filter residue rinsed thoroughly with ethyl acetate. The organic phase of the filtrate is separated and the aqueous phase re-extracted several times with ethyl acetate. The combined organic phases are dried over sodium sulfate and concentrated under vacuum. The residue is chromatographed on aluminum oxide (neutral, stage III) with a mixture of ethyl acetate and hexane, thus isolating 23.4 g of 110-(4-isopropenylphenyl)-5α-hydroxy-3,3-(2,2-dimethyltrimethylenedioxy)-9-estren-17-one as a white foam.

$^1$H-NMR (CDCl$_3$): δ=0.5 ppm (s,3H,H-18); 2.13 (s,3H, CH$_3$-olefin.); 4.3 (d J=6.5 Hz, 1H,H-11); 5.04 (s,1H,H-olefin.); 5.39 (s,1H,H-olefin.); 7.17 (d J=8 Hz, 2H,H-aromat.); 7.37 (d J=8 Hz, 2H,H-aromat.).

IR (KBr): 1740 cm$^{-1}$ five-ring ketone.

(c) 5 g of the steroid obtained in (b) is dissolved in 150 ml of absolute tetrahydrofuran and combined, in succession, with 17.15 g of potassium tert-butylate and 5.8 ml of 3-butyn-1-ol under a protective gas at 0° C. The reaction mixture is then allowed to warm up gradually to room temperature overnight, poured on saturated ammonium chloride solution, and the aqueous phase is repetedly extracted with ethyl acetate. The combined organic phases are dried over sodium sulfate and concentrated under vacuum. The residue is chromatographed on aluminum oxide (neutral, stage III) with a mixture of ethyl acetate/hexane, thus isolating 4.2 g of 17-(4-hydroxybut-1-ynyl)-11β-(4-isopropenylphenyl)-3,3-(2,2-dimethyltrimethylenedioxy)-9-estrene-5α,17β-diol as a white foam.

IR (KBr): 2220 cm$^{-1}$ triple bond.

(d) Analogously to the directions given in Example 1 under (b), 4 g of the compound produced in (c) is reduced, thus isolating 3.95 g of 17-(4-hydroxybut-1(Z)-enyl)-11β-(4-isopropenylphenyl)-3,3-(2,2-dimethyltrimethylenedioxy)-9-estrene-5α,17β-diol as a foamy crude product.

$^1$H-NMR (CDCl$_3$): δ=0.53 ppm (s,3H,H-18); 2.13 (s,3H, CH$_3$-olefin.); 4.26 (d J=6.5 Hz, H-11); 5.04 (s,1H,H-olefin.); 5.38 (s,1H,H-olefin.); 5.5 (m,1H,H-olefin. C-21); 5.69 (d J=11 Hz, H-olefin. C-20); 7.1–7.45 (m,4H,H-aromat.).

EXAMPLE 3

17-Methoxymethyl-17β-hydroxy-11β-(4-isopropenylphenyl)-4,9-estradien-3-one

In analogy to the acidic cleavage described in Example 1, 3 g of 17-methoxymethyl-11β-(4-isopropenylphenyl)-3,3 (2,2-dimethyltrimethylenedioxy)-9-estrene-5α,17β-diol is converted into 1.48 g of the desired compound.

$^1$H-NMR (CDCl$_3$): δ=0.56 ppm (s,3H,H-18); 2.13 (s,3H, CH$_3$-olefin.); 3.22 (d J=9.5 Hz, 1H,H-20); 3.43 (s,3H, CH$_3$-O); 3.57 (d J=9.5 Hz, 1H, H-20); 4.38 (d J=6.5 Hz, 1H,H-11); 5.06 (s,1H,H-olefin.); 5.38 (s,1H,H-olefin.); 5.77 (s,1H,H-4); 7.14 (d J=8 Hz, 2H,H-aromat.); 7.39 (d J=8 Hz, 2H,H-aromat.)

The starting material is produced as follows:

(a) Under a protective gas, 15 g of the intermediate product prepared in Example 2, directions under (b), is dissolved in 300 ml of absolute dimethylformamide and, at 0° C., combined in succession with 31.2 g of trimethylsulfonium iodide and 18 g of potassium tert-butylate. The reaction mixture is then warmed up gradually to room temperature under agitation overnight, thereafter poured on saturated ammonium chloride solution, and the aqueous phase is repeatedly extracted with ethyl acetate. The combined organic phases are dried over sodium sulfate, concentrated under vacuum, and the residue is chromatographed with a mixture of ethyl acetate/hexane on aluminum oxide (neutral, stage III), thus isolating 13.4 g of 11β-(4-isopropenylphenyl)-3,3-(2,2-dimethyltrimethylenedioxy)-9-estrene-[17(β-1)spiro-3]oxiran-5α-ol as a white foam.

$^1$H-NMR (pyridine-d$_5$): δ=0.64 ppm (s,3H,H-18); 2.07 (s,3H,CH$_3$-olefin.); 2.95 (d J=5 Hz, 1H,H-20); 2.95 (d J=5 Hz, 1H,H-20); 4.36 (d J=6 Hz, 1H,H-11); 5.01 (s,1H,H-olefin.); 5.07 (s,1H,H-olefin.); 7.32 (d J=8.5 Hz, 2H,H-aromat.); 7.53 (d J=8.5 Hz, 2H,H-aromat.).

(b) Under a protective gas, 5 g of the compound prepared in (a) is dissolved in 100 ml of a 3-molar methanolic sodium methylate solution and then heated to reflux for 3 hours. After cooling to room temperature, the reaction mixture is poured on water and the aqueous phase extracted repeatedly with ethyl acetate. The combined organic phases are dried over sodium sulfate and the solvents are evaporated under vacuum. The residue is chromatographed on aluminum oxide (neutral, stage III) with a mixture of ethyl acetate/hexane, thus isolating 4.5 g of 17-methoxymethyl-(4-isopropenylphenyl)-3,3-(2,2-dimethyltrimethylenedioxy)-9-estrene-5α,17β-diol as a white foam.

$^1$H-NMR (CDCl$_3$): δ=0.5 ppm (s,3H,H-18); 2.13 (s,3H, CH$_3$-olefin.); 3.48 (s,3H, CH$_3$-O); 4.25 (d J=6 Hz, 1H,H-11); 5.04 (s,1H,H-olefin.); 5.38 (s,1H,H-olefin.); 7.17 (d J=8.5 Hz, 2H,H-aromat.); 7.36 (d J=8.5 Hz, 2H,H-aromat.).

EXAMPLE 4

17-Cyanomethyl-17β-hydroxy-11β-(4-isopropenylphenyl)-4,9-estradien-3-one

Analogously to the acidic cleavage described in Example 1, 3 g of 17-cyanomethyl-11β-(4-isopropenylphenyl)-3,3-(2,2-dimethyltrimethylenedioxy)-9-estrene-5α,17β-diol yields 1.5 g of the desired compound.

$^1$H-NMR (CDCl$_3$): δ=0.6 ppm (s,3H,H-18); 2.14 (s,3H, CH$_3$-olefin.); 4.44 (d J=6 Hz, 1H, H-11); 5.07 (s,1H,H-olefin.); 5.38 (s,1H,H-olefin.); 5.79 (s,1H,H-4); 7.13 (d J=8 Hz, 2H,H-aromat.); 7.41 (d J=8 Hz, 2H,H-aromat.)

IR(KBr): 2260 cm$^{-1}$ nitrile.

The preparation of the starting material takes place in the following way:

(a) Under a protective gas, 5 g of the compound prepared as per Example 3, directions (a), is dissolved in 100 ml of ethanol and combined with a solution of 15 g of potassium cyanide in 33 ml of water. Subsequently the reaction mixture is heated overnight to 50° C., then poured on ice water, and the aqueous phase is extracted repeatedly with ethyl acetate. The combined organic phases are dried over sodium sulfate and concentrated under vacuum. The residue is chromatographed on aluminum oxide (neutral, stage III) with a mixture of ethyl acetate and hexane, thus obtaining 4 g of 17-cyanomethyl-11β-(4-isopropenylphenyl)-3,3-(2,2-dimethyltrimethylenedioxy)-9-estrene-5α,17β-diol as a white foam.

$^1$H-NMR (CDCl$_3$): δ=0.52 ppm (s,3H,H-18); 2.13 (s,3H, CH$_3$-olefin.); 4.32 (d J=6.5 Hz, 1H,H-11); 5.04 (s,1H,H-olefin.); 5.39 (s,1H,H-olefin.); 7.15 (d J=8 Hz, 2H,H-aromat.); 7.39 (d J=8 Hz, 2H,H-aromat.)

IR (KBr): 2250 cm$^{-1}$ nitrile.

EXAMPLE 5

17-(Prop-1-ynyl)-17β-hydroxy-11β-(4-isopropenylphenyl)-4,9-estradien-3-one

Analogously to the acidic cleavage disclosed in Example 1, 2.5 g of 17-(prop-1-ynyl)-11β-(4-isopropenylphenyl)-3,3-(2,2-dimethyltrimethylenedioxy)-9-estrene-5α,17β-diol yields 1.36 g of the desired compound.

$^1$H-NMR (CDCl$_3$): δ=0.52 ppm (s,3H.H-18); 1.77 (s,3H,H-22); 2.13 (s,3H, CH$_3$-olefin.); 4.43 (d J=6.5 Hz, 1H,H-11); 5.05 (s,1H,H-olefin.); 5.37 (s,1H,H-olefin.); 5.78 (s.1H,H-4); 7.13 (d J=8 Hz, 2H,H-aromat.); 7.4 (d J=8 Hz, 2H,H-aromat.).

The starting material is prepared as follows:

(a) 150 ml of absolute tetrahydrofuran is saturated with methylacetylene by introducing the latter for 30 minutes at 0° C. Then, at a temperature of between 0° and 5° C., 19 ml of a 15% strength solution of n-butyllithium in hexane is added dropwise thereto; after this step, the mixture is stirred for 15 minutes and then a solution of 3 g of the ketone obtained in Example 2(b) in 25 ml of absolute tetrahydrofuran is gradually added. The reaction mixture is stirred for 2 hours, poured on water, and the aqueous phase is extracted reeeatedly with ethyl acetate. The combined organic phases are dried over sodium sulfate and concentrated under vacuum. The residue is chromatographed with a mixture of ethyl acetate/hexane on aluminum oxide (neutral, stage III), thus obtaining 2.73 g of 17-(prop-1-ynyl)-11β-(4-isopropenylphenyl)-3,3-(2,2-dimethyltrimethylenedioxy)-9-estrene-5α,17β-diol as a white foam.

IR (KBr): 2230 cm$^{-1}$ triple bond.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11 β-(4-isopropenylphenyl)estra-4,9-diene of the formula

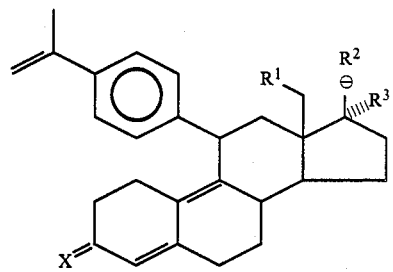

wherein
X is O or N~~~OH,
R$^1$ is hydrogen or methyl,
R$^2$ is hydrogen, C$_{1-10}$-alkanoyl or benzoyl,
R$^3$ is hydrogen, cyanomethyl, —(CH$_2$)$_n$—CH$_2$Z, —CH=CH—(CH$_2$)$_m$Z or —C≡C—Y—,
n=0 to 5,
m=1 to 4,
Z is hydrogen or OR$^4$,
R$^4$ is hydrogen, C$_{1-4}$-alkyl or C$_{1-4}$ alkanoyl, and
Y is hydrogen, chlorine, fluorine, iodine, bromine, C$_{1-4}$-alkyl, hydroxy-C$_{1-4}$-alkyl, C$_{1-4}$-alkoxy-C$_{1-4}$-alkyl or acyloxy-C$_{1-4}$-alkyl wherein acyl is C$_{1-4}$-alkanoyl or benzoyl.

2. A compound of claim 1 wherein X is 0.
3. A compound of claim 1 wherein X is N~~~OH.
4. A compound of claim 1 wherein R$^1$ is H.
5. A compound of claim 1 wherein R$^1$ is CH$_3$.
6. A compound of claim 1 wherein R$^2$ is H.
7. A compound of claim 1 wherein R$^2$ is C$_{1-4}$-alkanoyl.
8. A compound of claim 1 wherein R$^3$ is H.
9. A compound of claim 1 wherein R$^3$ is —CH$_2$CN.
10. A compound of claim 1 wherein R$^3$ is —(CH$_2$)$_n$CH$_2$Z.
11. A compound of claim 1 wherein R$^3$ is —CH=CH(CH$_2$)$_m$Z.
12. A compound of claim 1 wherein R$^3$ is —C≡C—Y.
13. 11 β-(4-Isopropenylphenyl)-17 β-hydroxy-4,9-estradien-3-one,
11 β-(4-isopropenylphenyl)-17 β-hydroxy-17-(prop-1-ynyl)-4,9-estradien-3-one, 11 β-(4-isopropenylphenyl)-17 β-hydroxy-17-(prop-1(Z)-enyl)-4,9-estradien-3-one,
11 β-(4-isopropenylphenyl)-17 β-hydroxy-17-methoxymethyl-4,9-estradien-3-one,
11 β-(4-isopropenylphenyl)-17 β-hydroxy-17-cyanomethyl-4,9-estradien-3-one,
11 β-(4-isopropenylphenyl)-17 β-hydroxy-17-(3-hydroxyprop-1(Z)-enyl)-4,9-estradien-3-one,
11 β-(4-isopropenylphenyl)-17 β-hydroxy-17-(4-hydroxybut-1(Z)-enyl)-4,9-estradien-3-one,
11 β-(4-isopropenylphenyl)-17 β-hydroxy-1β-methyl-4,9-estradien-3-one,
11 β-(4-isopropenylphenyl)-17 β-hydroxy-1β-methyl-17-(prop-1-ynyl)-4,9-estradien-3-one,
11 β-(4-isopropenylphenyl)-17 β-hydroxy-1β-methyl-17-(prop-1(Z)-enyl)-4,9-estradien-3-one,
11 β-(4-isopropenylphenyl)-17 β-hydroxy-1β-methyl-17-(3-hydroxyprop-1(Z)-enyl)-4,9-estradien-3-one,
11 β-(4-isopropenylphenyl)-17 β-hydroxy-1β-methyl-17-(4-hydroxybut-1(Z)-enyl)-4,9-estradien-3-one,
11 β-(4-isopropenylphenyl)-17 β-hydroxy-17-(3-hydroxypropyl)-4,9-estradien-3-one, or
11 β-(4-isopropenylphenyl)-17 β-hydroxy-18-methyl-17-(3-hydroxypropyl)-4,9-estradien-3-one, each a compound of claim 1.

14. A pharmaceutical composition comprising an antiprogestationally effective amount of a compound of claim 1 and a pharmaceutically acceptable carrier.

15. A composition of claim 14 wherein the amount of said compound is 1–100 mg.

16. A method of achieving an antiprogestational effect in a patient in need of such treatment comprising administering to said patient an antiprogestationally effective amount of a compound of claim 1.

17. A method of claim 16 wherein said effect is a post-coital abortion.

18. A method of claim 16 wherein said effect is treatment of a hormonal irregularity or induction of menstruation.

* * * * *

UNITED STATES PATENT AND TRADEMARK OFFICE
CERTIFICATE OF CORRECTION

PATENT NO. : 4,814,327

DATED : March 21, 1989

INVENTOR(S) : Eckhard Ottow et al

It is certified that error appears in the above-identified patent and that said Letters Patent is hereby corrected as shown below:

Column 12, line 41: reads "$-CH=CH-(CH_2)_m Z$ or $-C\equiv C-Y-$,"

should read -- $-CH=CH-(CH_2)_m Z$ or $-C\equiv C-Y$, --

Column 13, lines 11, 13, 15, 17 and 19:
reads "B-(4-ispopropenylpheny)-17 B-hydroxy-1B-methyl-"
should read -- B-(4-isopropenylphenyl)-17 B-hydroxy-18-methyl- --

Signed and Sealed this

Twenty-third Day of January, 1990

Attest:

JEFFREY M. SAMUELS

Attesting Officer    Acting Commissioner of Patents and Trademarks